United States Patent [19]

Morrison

[11] 4,197,646
[45] Apr. 15, 1980

[54] HOUSING FOR DENTAL AMALGAMATOR

[76] Inventor: Paul M. Morrison, 9004 Copenhaver Dr., Potomac, Md. 20854

[21] Appl. No.: 857,555

[22] Filed: Dec. 5, 1977

[51] Int. Cl.² ............................................. A61C 19/02
[52] U.S. Cl. ...................................... 433/97; 366/139; 98/115 R
[58] Field of Search ............. 32/40 A, 40 R; 366/139, 366/347, 602; 98/115 R; 422/104; 312/209, 1

[56] References Cited

U.S. PATENT DOCUMENTS

| | | | |
|---|---|---|---|
| 2,013,498 | 9/1935 | McConaughy | 98/115 R |
| 2,397,731 | 4/1946 | Fowler | 98/115 R |
| 2,453,914 | 11/1948 | Hollenback | 366/139 |
| 2,799,935 | 7/1957 | Hall | 32/40 A |
| 2,931,633 | 4/1960 | Rumbel et al. | 366/139 |
| 3,072,040 | 1/1963 | Triplett | 98/115 R |
| 4,059,903 | 11/1977 | Piet et al. | 32/40 R |
| 4,071,338 | 1/1978 | Hutter et al. | 98/115 R |
| 4,108,509 | 8/1978 | Piet et al. | 32/40 R |

Primary Examiner—Louis G. Mancene
Assistant Examiner—John J. Wilson
Attorney, Agent, or Firm—John C. Smith, Jr.

[57] ABSTRACT

A housing for containing a dental amalgamator is adapted both to retain liquid mercury lost during operation of the amalgamator such that the liquid mercury may be recovered and confine mercury vapor evolved during amalgamation and exhaust the mercury vapor safely without contaminating the atmosphere of the room or dental office in which the amalgamator is located. The housing includes an opening for access to the amalgamator to insert and remove the mortar and pestal, the opening being normally sealed by a removable closure.

10 Claims, 5 Drawing Figures

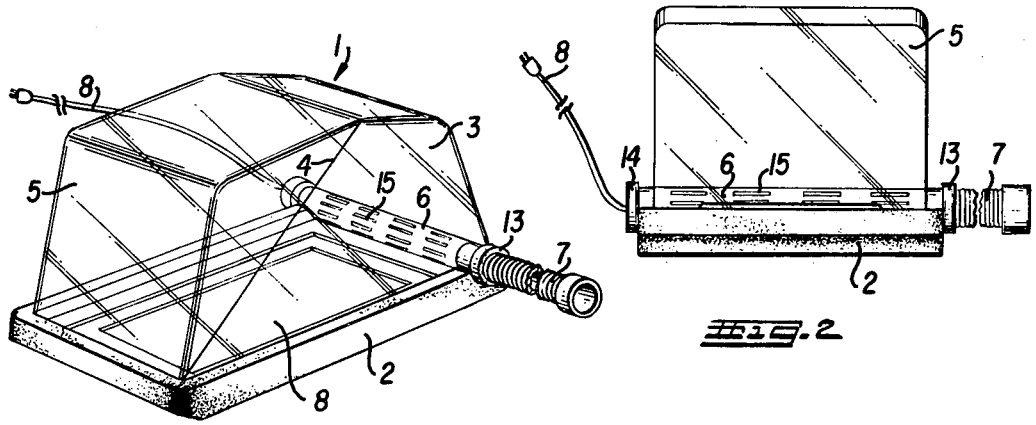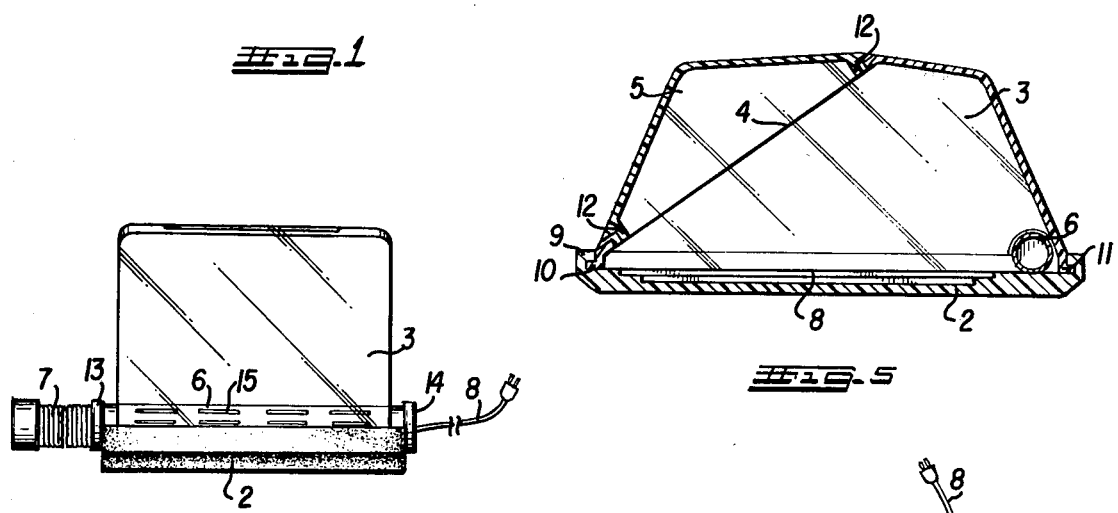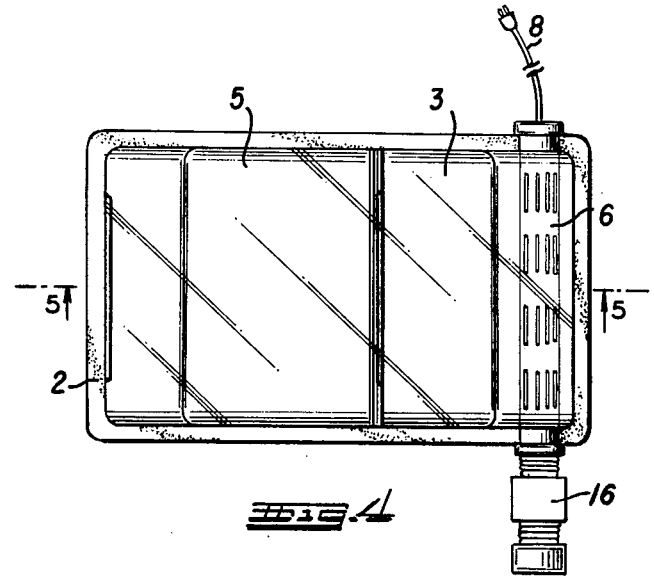

ced. The opening 4 is

HOUSING FOR DENTAL AMALGAMATOR

BACKGROUND OF THE INVENTION

The present invention is concerned with a housing designed for containing and enclosing a dental amalgamator used in dental offices. The housing is adapted to retain liquid mercury which is inevitably lost during operation of the amalgamator such that the liquid mercury may be recovered. The housing is also adapted to confine mercury vapor generated during operation of the amalgamator and to exhaust the mercury vapor to avoid contamination of the atmosphere of the room or dental office in which the amalgamator is located.

In recent years the dental profession and those concerned with occupational safety have become increasingly aware and concerned with the problem of mercury contamination in dental offices. The dental profession is one of the large consumers of mercury metal which is used in amalgams containing mercury, silver and other optional metals to fill cavities in teeth. Though the amalgams are soft at first, they form hard, lasting fillings. The amalgams are commonly produced in dental offices by placing the mercury, silver and optional other metals in a mortar or capsule which usually also contains a small pestle or pellet. The mortar is secured in an electrically driven agitating device or amalgamator which causes the pestle to be oscillated within the mortar providing an effective triturating or grinding action to form the amalgam. U.S. Pat. Nos. 2,201,428; 2,286,599 and 2,286,600, all to E. L. Chott and incorporated by reference in the present disclosure, describe in detail various mortar and pestle designs and dental amalgamators.

Mercury toxication is frequently encountered by dentists and other personnel who regularly inhabit dental offices and prepare amalgams for use in filling teeth. The mercury toxication is from two sources, namely, direct absorption of liquid mercury into the body through contact or handling of mercury and mercury containing compounds and through inhalation of vapor emitted during the amalgamation process when mercury and mercury-containing substances are volatilized. The problems of mercury toxication in dental offices are described in detail in the *Journal of The American Dental Association*, Vol. 92, No. 6, (1976) in two articles entitled "Mercury Toxicity in the Dental Office: A Neglected Problem" by Manteyla et al. (pages 1189-1194) and "The Silent Hazard: An Unusual Case of Mercury Contamination of a Dental Suite" by Pagnotto et al. (pages 1195-1198). These articles are incorporated by reference in the present disclosure.

Liquid mercury frequently escapes from the mortar during the amalgamation process, contaminating work benches, rubs, equipment, etc. This lost liquid mercury becomes a potentially hazardous source of mercury vapor when it vaporizes into the atmosphere. Also as mentioned previously mercury vapor is evolved during amalgamation, further contaminating the atmosphere of the dental office.

Mercury contamination is hazardous to the health of those persons who are exposed to the liquid mercury and mercury vapor over an extended period of time. Symptoms of mercury toxication include erthism (a psychic disturbance), tremor, speech disorders, alteration of handwriting, motor and sensory nerve disorders, eye affections, oral pathosis, etc. Safety experts are generally agreed that the mercury vapor content of the ambient air must not be in excess of the threshold limit value of 0.05 mg/m$^3$.

Dentists and other dental personnel have been cautioned to avoid direct contact with mercury metal and spilling of mercury metal which may contaminate the ambient air due to vaporization. Construction of exhaust systems in dental offices to prevent recirculation of mercury vapor has been recommended. These precautions however, have not been completely effective in maintaining the ambient air mercury vapor level below the threshold limit value of 0.05 mg/m$^3$.

An object of the present invention is to reduce the risk of exposure of both liquid mercury and mercury vapor in dental offices.

A further object of the invention is to provide apparatus for isolating liquid mercury and mercury vapor from the ambient air in the dental office during operation of dental amalgamators.

SUMMARY OF THE INVENTION

The present invention provides an effective and economical means for controlling the loss of liquid mercury and contamination of the ambient air due to vaporization of mercury. More specifically the present invention serves to contain all liquid mercury which may escape from the mortar during operation of the dental amalgamator and to prevent the mercury vapor produced by the lost liquid mercury and by vaporization of mercury during the amalgamation process from contaminating the ambient air of the dental office.

More specifically the present invention comprises a housing for the dental amalgamator which is designed to retain any lost liquid mercury and to draw off any mercury vapor contaminated air within the housing before the mercury vapor can contaminate the ambient air of the dental office. The housing includes an opening adapted to be sealed when the amalgamator is in use permitting access to the amalgamator to position the mortar in the amalgamator prior to operation of the amalgamator and to remove the mortar after amalgamation has been completed.

BRIEF DESCRIPTION OF DRAWINGS

FIG. 1 is a perspective view of a housing for a dental amalgamator in accordance with the invention;

FIG. 2 is a front view of the housing shown in FIG. 1;

FIG. 3 is a rear view of the housing shown in FIG. 1;

FIG. 4 is a plan view of the housing shown in FIG. 1; and

FIG. 5 is a cross-sectional view of the housing shown in FIG. 4 taken along the line 5—5.

DETAILED DESCRIPTION OF THE INVENTION

The housing for a dental amalgamator shown generally at 1 comprises a tray or base member 2 on which is mounted a canopy 3. A dental amalgamator such as that described in U.S. Pat. Nos. 2,201,428; 2,286,599 and 2,286,600 to Chott is positioned on the tray 2 before the canopy 3 is secured to the tray. The canopy 3 is provided with an opening 4 for access to the dental amalgamator permitting the operator to position the mortar and pestle in the amalgamator prior to operation of the amalgamator and to remove the mortar and pestle after amalgamation has been completed. The opening 4 is normally sealed by a closure or lid 5. A perforated tubular member 6 extends across the rear of the tray 2 and is connected to a flexible hose 7 at one end thereof. The opposite end of the perforated tubular member 6 includes a seal through which an electric power cord 8 extends.

The various parts of the housing are preferably composed of flexible plastic materials. The canopy 3 and closure or lid 5 should be transparent providing the operator with an unobstructed view of the amalgamator.

The tray or base member 2 is of substantially heavier construction than the canopy 3 and closure 5. The central portion 8 of the tray which supports the amalgamator is recessed for the purpose of retaining any liquid mercury which may escape from the mortar and pestle during operation of the amalgamator. This arrangement permits the retained liquid mercury to be recovered from time to time. The perimeter of the tray 2 comprises an elevated portion 9 having an inwardly facing continuous groove 10. The opposite sides of the elevated portion 9 adjacent the rear of the tray are recessed to receive and position the perforated tubular member 6.

The canopy 3 includes an outwardly extending continuous lip 11 which is adapted to be received in the groove 10 of the tray to secure the canopy on the tray 2 and to assure an airtight seal therebetween. The canopy may be easily mounted on and removed from the tray due to the flexibility of the materials used in both the canopy and tray. The closure or lid 5 includes a continuous flange 12 about its perimeter which is adapted to engage the perimeter of the opening 4 in the canopy to retain the closure 5 in place. The closure may be easily removed for access to the dental amalgamator.

The perforated tubular member 6 is retained between the recesses in the elevated portion 9 at opposite sides adjacent the rear of the tray 2 and similar recesses at opposite sides adjacent the rear of the canopy 3. Flanges 13 and 14 at opposite ends of the perforated tubular member 6 engage the opposite sides of the tray 2 preventing the tubular member from sliding longitudinally. Perforations 13 are provided in the tubular member 6. The flexible hose 7 may be connected to any source of vacuum 16, which is commonly available in dental offices, to maintain the air pressure within the housing at less than atmospheric pressure. Air within the housing and any mercury vapor emitted either from the mortar and pestle or from the liquid mercury retained in the recessed central portion 8 of the tray is drawn through the perforations 15 in the tubular member 6 into the tubular member and through the flexible hose 7 where it is exhausted, thus avoiding mercury vapor contamination of the ambient air in the dental office. The electric power cord 8 serves to provide power to the dental amalgamator contained within the housing.

In an alternative embodiment the perforated tubular member 6 may contain a rotatably mounted fan driven by an electric motor located within or adjacent to the flange 14 at the closed end of the tubular member 6. The electric power cord 8 provides power for both the fan motor and the amalgamator. In this embodiment the flexible hose 7 may lead out of the building in which the dental office is located whereby the mercury vapor contaminated air, drawn from the housing into the perforated tubular member 6, is exhausted through flexible hose 7 into the outdoor atmosphere to avoid contamination of the ambient air in the dental office.

While various modifications of the above described device have been described it is obvious that further modifications and changes may be made within the scope of the invention and without departing from the spirit thereof.

I claim:

1. A housing for a dental amalgamator comprising:
   (a) a base tray member of flexible material and having a central portion surrounded by a perimeter portion, said central portion being horizontally disposed and recessed with respect to said perimeter portion for supporting said dental amalgamator and for retaining any liquid mercury lost from said amalgamator;
   (b) a canopy supported about its perimeter by said perimeter portion of said tray member and adapted to cover said dental amalgamator, said canopy including an opening therein for access to said dental amalgamator;
   (c) a removable closure covering and sealing said opening in said canopy;
   (d) means for releasably securing and sealing together the perimeter of said canopy and said perimeter portion of said tray member, said securing and sealing means comprising a groove in said perimeter portion of said tray member for receiving therein the perimeter edge of said canopy; and
   (e) an air duct extending from said housing for exhausting air and any mercury vapor from the interior of said housing and thereby maintaining a pressure less than atmospheric in said housing.

2. A housing as defined in claim 1 wherein said perimeter edge of said canopy includes a lip projecting radially in a plane substantially parallel to the plane of said tray member, and the open side of said groove in said perimeter portion of said tray member faces inwardly to receive said canopy lip.

3. A housing as defined in claim 2 further comprising blower means for drawing air with any mercury vapor contained therein from the interior of said housing and exhausting said withdrawn air through said air duct.

4. A housing as defined in claim 1 further comprising an elongated tubular member supported on and extending across said tray member from one side thereof to the opposite side thereof, said tubular member having perforations in the wall thereof for transmitting air therethrough and said air duct being connected to one end of said tubular member, whereby air and any mercury vapor are drawn from the interior of said housing, through said perforations in said wall of said tubular member into the interior of said tubular member and are exhausted through said air duct.

5. A housing as defined in claim 4 wherein said tubular member is retained between complimentary notches in said perimeter portion of said tray member at opposite sides of said tray member and in said canopy at opposite sides thereof.

6. In combination, a dental amalgamator for preparing dental alloys and a housing for retaining any lost liquid mercury from said amalgamator and exhausting mercury vapor, said housing comprising:
   (a) a base tray member of flexible material and having a central portion surrounded by a perimeter portion, said central portion being horizontally disposed and recessed with respect to said perimeter portion and supporting said dental amalgamator;
   (b) a canopy supported about its perimeter on said perimeter portion of said tray member and covering said dental amalgamator, said canopy including an opening therein for access to said dental amalgamator;

(c) a removable closure covering and sealing said opening in said canopy;

(d) means for releasably securing and sealing together the perimeter of said canopy and said perimeter portion of said tray member, said securing and sealing means comprising a groove in said perimeter portion of said tray member for receiving therein the perimeter edge of said canopy; and (e) an air duct extending from said housing for exhausting air and any mercury vapor from the interior of said housing and thereby maintaining a pressure less than atmospheric in said housing.

7. The combination as defined in claim 6 wherein the perimeter edge of said canopy includes a lip projecting radially in a plane substantially parallel to the plane of said tray member, and the open side of said groove in said perimeter portion of said tray member faces inwardly to receive said canopy lip.

8. The combination as defined in claim 7 further comprising blower means for drawing air with any mercury vapor contained therein from the interior of said housing and exhausting said withdrawn air through said air duct.

9. The combination as defined in claim 6 further comprising an elongated tubular member supported on and extending across said tray member from one side thereof to the opposite side thereof, said tubular member having perforations in the wall thereof for transmitting air therethrough and said air duct being connected to one end of said tubular member, whereby air and any mercury vapor are drawn from the interior of said housing, through said perforations in said wall of said tubular member into the interior of said tubular member and are exhausted through said air duct.

10. The combination as defined in claim 9 wherein said tubular member is retained between complimentary notches in said perimeter portion of said tray member at opposite sides of said tray member and in said canopy at opposite sides thereof.

* * * * *